United States Patent [19]

Findeisen

[11] 4,284,584
[45] Aug. 18, 1981

[54] PROCESS FOR THE PREPARATION OF ACYL CYANIDES

[75] Inventor: Kurt Findeisen, Odenthal, Fed. Rep. of Germany

[73] Assignee: Bayer Aktiengesellschaft, Leverkusen, Fed. Rep. of Germany

[21] Appl. No.: 967,932

[22] Filed: Dec. 8, 1978

Related U.S. Application Data

[63] Continuation of Ser. No. 777,286, Mar. 11, 1977, abandoned.

[30] Foreign Application Priority Data

Apr. 2, 1976 [DE] Fed. Rep. of Germany ....... 2614240

[51] Int. Cl.$^3$ .................. C07C 51/54; C07C 63/04
[52] U.S. Cl. .................. 260/545 R; 260/326.5 J; 260/465 R; 260/465.1; 260/347.8; 544/106; 548/128; 548/215; 548/240; 548/225; 548/212; 548/335; 548/341; 548/346; 548/373; 548/375; 548/377; 548/378; 546/184; 546/225
[58] Field of Search .......... 260/545 R, 347.8, 326.5 J, 260/307 H, 307 R, 307 D, 308 A, 308 B, 465, 465 R, 465.1; 544/106; 548/335, 337, 338, 339, 373, 375, 377, 378, 335, 128; 560/155, 19, 125

[56] References Cited

PUBLICATIONS

Thesing et al., Angewandte Chemie, vol. 68, pp. 425–426, 434–435, (1956), (PTO Rough Translation Attached).

Erlenmeger, Liebigs Ann. Chem. vol. 287, pp. 302–310, (1895).

Migrdichian, "Organic Synthesis" vol. 1, pp. 291–292, (1957).

*Primary Examiner*—Howard T. Mars
*Attorney, Agent, or Firm*—Sprung, Felfe, Horn, Lynch & Kramer

[57] ABSTRACT

Acyl cyanides of the formula

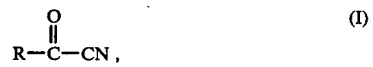

in which
  R represents alkyl or substituted alkyl of from 1 to 8 carbon atoms, cycloalkyl or substituted cycloalkyl of from 3 to 12 carbon atoms, aryl or substituted aryl; or an optionally substituted 5-membered or 6-membered heterocyclic radical which can also be fused with a benzene ring are prepared by reacting the corresponding carboxylic acid anhydride in the presence of a carboxylic acid halide with an alkali metal cyanide or anhydrous acid, at a temperature of between 50° and 300° C.

18 Claims, No Drawings

PROCESS FOR THE PREPARATION OF ACYL CYANIDES

This is a continuation of application Ser. No. 777,286 filed Mar. 11, 1977, now abandoned.

The present invention relates to a process for the preparation of certain acyl cyanides. Such compounds are useful as starting materials for the synthesis of herbicides.

It is known that acyl cyanides can be prepared by reacting acyl halides with metal cyanides (compare Angew. Chem. 68, 425-448 (1956)). However, this process has a number of disadvantages. Thus, for example, it is expensive and can be carried out technically only with difficulty since it is a two-phase reaction in which a solid is reacted with a liquid or with a substance present in solution. Moreover, the reaction does not give a single reaction product but a mixture of substances which is difficult to separate and which also contains, in addition to the particular acyl cyanide, a relatively large amount of a corresponding dimer. Accordingly, the yields of the acyl cyanide are relatively low. A further disadvantage of this process is that the washing water obtained during working up has to be subjected to thorough purification before it is run off since it still contains considerable amounts of highly toxic metal cyanides which are used in excess during the reaction.

Furthermore, it is known that aroyl cyanides can be synthesized by reacting arylcarboxylic acid chlorides with hydrocyanic acid, in the presence of pyridine as an acid-binding agent, in absolute ether (see Angew. Chem. 68, 425-448 (1956)). However, this process also is associated with several disadvantages. Thus, firstly, it is not generally applicable. Moreover, it is technically very involved because the operations with pyridine, which is highly toxic, and with ether, which is readily inflammable, demand particularly stringent safety precautions. Moreover, in this case also through purification of the washing water obtained during working up is unavoidable because of the pyridine dissolved therein. The fact that a considerable amount of dimeric aroyl cyanide is formed during the reaction is also a disadvantage since, as a result of this, both the yield of aroyl cyanide is greatly reduced and the isolation thereof is made more difficult.

It is also known to react benzoic acid anhydride with potassium cyanide in an equivalent amount and this reaction gives benzoyl cyanide in a low yield (about 10% of theory) (Liebigs Annalen der Chemie 287, page 306 (1895)). The benzoyl cyanide must be removed with ether from the viscous, very highly resinified, dark brown mass which is formed as the main product. This process is technically completely unsuitable, since not only the extraction with ether leads to difficulties which cannot be overcome technically but there is also no further use for the very highly resinified dark brown masses. This method is, therefore, merely a possible means of forming benzoyl cyanide.

The present invention now provides a process for the preparation of an acyl cyanide of the general formula

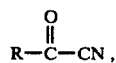  (I)

in which
R represents alkyl or substituted alkyl of from 1 to 8 carbon atoms; cycloalkyl or substituted cycloalkyl with 3 to 12 ring carbon atoms; aryl or substituted aryl; or an optionally substituted 5-membered or 6-membered heterocyclic radical which can additionally
also be fused with a benzene ring, in which a carboxylic acid anhydride of the general formula

R—CO—O—CO—R  (II), in which
R has the above-mentioned meaning, is reacted, in the presence of a compound of the general formula

R—X  (III), in which
R has the above-mentioned meaning and
X represents a —COCl, —COF, —COBr, —CCl$_3$, —CF$_3$, —CBr$_3$, —CHCl$_2$, —CHF$_2$ or CHBr$_2$ group,
with an alkali metal cyanide or anhydrous hydrocyanic acid, optionally in the presence of a diluent, at a temperature of between 50° and 300° C.

By means of this invention, the acyl cyanides (I) can be obtained in very high yield and excellent purity in a "one-pot reaction".

Preferably, R represents straight-chain or branched alkyl with 1 to 4 carbon atoms, which can optionally be substituted by one or more substituents selected from alkoxy with 1 to 4 carbon atoms, carbalkoxy with 1 to 4 carbon atoms in the alkyl part, nitro, nitrile and halogen (namely fluorine, chlorine, bromine and iodine); cycloalkyl with 5 or 6 carbon atoms in the ring system and which optionally carries one or more substituents selected from alkyl with 1 to 4 carbon atoms, alkoxy or carbalkoxy with, in either case, up to 4 carbon atoms in the alkyl part, nitro, nitrile and halogen (for example fluorine, chlorine and bromine); phenyl or naphthyl, either of which can optionally carry one or more substituents selected from alkyl with 1 to 4 carbon atoms, alkoxy or carbalkoxy with, in either case, up to 4 carbon atoms in the alkyl part, nitro and halogen (for example fluorine, chlorine and bromine); or a 5-membered or 6-membered heterocyclic radical which can contain 1 to 3 hetero-atoms, selected from oxygen, sulphur and nitrogen atoms, in the ring and which optionally carries one or more substituents selected from alkyl with 1 to 4 carbon atoms, alkoxy or carbalkoxy with, in either case, up to 4 carbon atoms in the alkyl part, nitro, nitrile and halogen (for example fluorine, chlorine and bromine) and which can optionally be fused to a benzene ring.

Examples which may be mentioned of the heterocyclic radicals R are morpholinyl, imidazolyl, pyrazolyl, pyrrolyl, isoxazolyl, piperidinyl, oxazolyl, 1,2,4-triazol-1-yl, 1,2,4-triazol-4-yl, 1,2,3-triazolyl, 1,2,4-thiadiazol-2-yl, benzimidazolyl and furanyl.

It has furthermore been found that the carboxylic acid anhydrides (II) can also be produced in the reaction mixture (in the nascent state), for example by reacting alkali metal salts of the corresponding carboxylic acids with the corresponding acid halides. Thus, for example, benzoic acid anhydride can be prepared in the reaction mixture from sodium benzoate and benzoyl chloride.

It is to be regarded as extremely surprising that acyl cyanides of the formula (I) are accessible in high yield and excellent purity by the process according to the invention since, in view of the known state of the art, it was to be expected that either the same difficulties would arise with this process as in the case of the reaction of acyl halides with alkali metal cyanides or metal cyanides in a two-phase system or that the desired acyl cyanide would be formed only in traces. In particular, it was in no way to be foreseen that the formation of undesired dimeric acyl cyanides or resinous products would not take place at all.

The process according to the invention has a number of advantages. Thus, it is not restricted to the synthesis of a few specific compounds that has very broad application, especially in the aromatic series. The one-pot process is a significant enrichment of the art since separate working up of alkali metal salts of the carboxylic acids is avoided, the reaction temperature is lowered, the carboxylic acid anhydride is recovered virtually quantitatively and the carboxylic acid halide group can even by replaced by trihalogenomethyl and dihalogenomethyl groups.

The process can give acyl cyanides in virtually quantitative yield and excellent purity, free from by-products which are troublesome or pollute the environment. An additional important advantage of the process according to the invention is that working up presents no problems. The alkali metal halide formed in the course of the reaction is filtered off and the acyl cyanide is distilled. The carboxylic acid anhydride can be re-used without purification.

If hydrocyanic acid is used in place of the alkali metal cyanides, hydrogen chloride is formed as the by-product and this can be put to diverse further uses in chemistry.

If benzoic acid anhydride, anhydrous hydrocyanic acid (or sodium cyanide) and benzoyl chloride are used as the starting materials, the course of the reaction can be represented by the following equation:

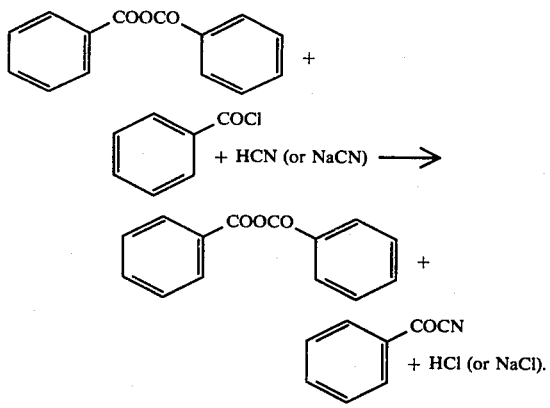

When benzotrichloride or benzal chloride is used the course of the reaction can be represented by the following equations:

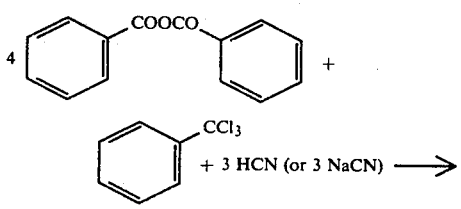

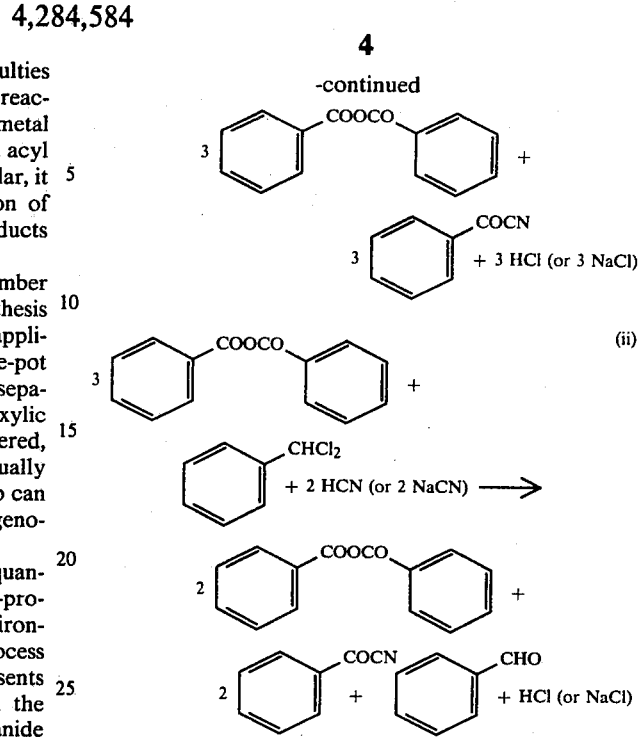

Both the acid anhydrides that are used as starting materials, and which are generally defined by the formula (II) above, and the compounds RX (that is to say acid halides and trihalogenomethyl and dihalogenomethyl compounds) defined by the formula (III) above can be synthesised by known methods.

Preferred examples of carboxylic acid anhydrides of the formula (II) which may be mentioned are: acetic anhydride, propionic anhydride, pivalic anhydride, cyclohexanecarboxylic acid anhydride, benzoic acid anhydride, m-chlorobenzoic acid anhydride, 3,5-dichlorobenzoic acid anhydride, naphthalene-1-carboxylic acid anhydride and 1-phenyl-5-pyrazolone-3-carboxylic acid anhydride. Particularly preferred anhydrides which may be mentioned are the aromatic carboxylic acid anhydrides, especially benzoic acid anhydride.

Preferred carboxylic acid halides according to formula (III) which may be mentioned are: acetyl chloride, acetyl bromide, propionyl chloride, propionyl bromide, cyclohexanecarboxylic acid chloride (bromide), cyclopentanecarboxylic acid chloride (bromide), benzoyl fluoride, benzoyl bromide, benzoyl chloride, m-chlorobenzoyl chloride, 3,5-dichloro-benzoyl chloride, naphthalene-1-carboxylic acid chloride, 1-phenyl-5-pyrazolone-3-carboxylic acid chloride, terephthalic acid dichloride, isophthalic acid dichloride and others. Benzoyl chloride may be mentioned as a particularly preferred acid chloride.

Particularly preferred dihalogenomethyl and trihalogenomethyl compounds according to formula (III) which may be mentioned are: benzotrichloride, benzal chloride, o-, m- and p-chlorobenzotrichloride, 2,4-dichlorobenzal chloride, benzotrifluoride and benzotribromide.

Particularly preferred alkali metal cyanides which may be mentioned are sodium cyanide and potassium cyanide.

Possible diluents which can be employed when carrying out the process according to the invention are all inert organic solvents which do not enter into a chemical reaction with either the carboxylic acid anhydrides, or the compounds of the formula (III) or the metal cyanides or hydrocyanic acid. Examples of such solvents are the xylenes, such as o-xylene, chlorobenzene, o-dichlorobenzene, the trichlorobenzenes, nitrobenzene and tetramethylenesulphone. An excess of the carboxylic acid anhydride (II) is particularly suitable as a diluent. In principle, however, it is also possible to carry out the reaction according to the invention without diluents.

The reaction temperature can be varied within a fairly wide range. In general, the reaction is carried out at temperatures of between 50° and 300° C. and preferably of between 80° and 280° C.

The reaction is generally carried out under normal pressure. When low-boiling aliphatic carboxylic acid anhydrides are used, however, a slight excess pressure is advantageous and the excess pressure is then, in general, from 1 to 10, and preferably from 1 to 5, atmospheres.

The reaction can be accelerated by adding catalytic amounts of a base or Lewis acid. Examples of suitable bases are tertiary amines, such as dimethylbenzylamine and 1,4-diazabicyclo[2.2.2]octane, and alkali metal salts of carboxylic acids, for example sodium benzoate. Examples of suitable Lewis acids which may be mentioned are zinc chloride, zinc cyanide, copper(I) cyanide, copper (II) cyanide, and Na$_3$[Cu(CN)$_4$].

When carrying out the process according to the invention, in general stoichiometric amounts of the acid anhydride are reacted with a compound of the formula (III), an alkali metal cyanide or anhydrous hydrocyanic acid. However, the acid anhydride can also be used in excess and in that case is advantageously even used as the solvent.

Working up is carried out after the reaction has ended, usually by filtration, distillation and, where appropriate, recrystallisation.

The mixture of the acid anhydride, a compound of the formula (III) and hydrocyanic acid can also be reacted, according to the invention, in the gas phase, without the special use of catalysts.

In a particular embodiment, the reaction according to the invention can also be utilised as a continuous reaction.

The acyl cyanides of the formula (I) which can be prepared by the process according to the invention are valuable starting materials, for example for the synthesis of 1,2,4-triazin-5-ones, which possess outstanding herbicidal properties (see German Offenlegungsschrift (German Published Specification) No. 2,224,161).

Thus, for example, 3-methyl-4-amino-6-phenyl-1,2,4-triazin-5-one of the formula

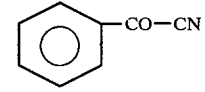

can be prepared by reacting benzoyl cyanide, in the presence of concentrated hydrochloric acid, with ethanol in a first stage and, in a second stage, reacting the resulting phenylglyoxylic acid ethyl ester with acetylhydrazine, whereupon 1-phenylglyoxylic acid ethyl ester-2-acetylhydrazone is formed, which, in a third stage, is converted, with hydrazine hydrate, in the presence of pyridine, into the abovementioned end product.

This multi-stage synthesis can be represented by the following equations:

1st stage:

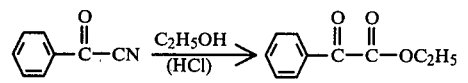

2nd stage:

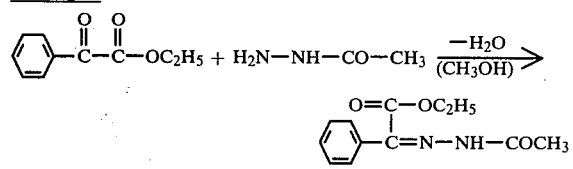

3rd stage:

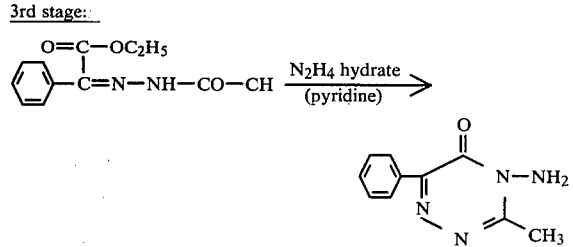

The process according to the invention is illustrated by the preparative Examples which follow:

EXAMPLE 1

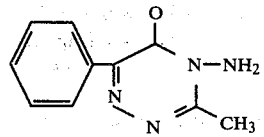
(1)

226.2 (1 mol) of benzoic acid anhydride, 140.6 g of benzoyl chloride and 50 g (1 mol) of 98% pure sodium cyanide were mixed in a 1 liter flask, whilst stirring. The mixture was warmed to 155° C. in the course of 30 minutes. A slightly exothermic reaction took place. After 10 minutes, the reaction was stirred for a further 30 minutes at 155°–160° C., by external heating, and the reaction was brought to completion. The reaction mixture was cooled to 90° C., a distillation apparatus was installed and the benzoyl cyanide formed was distilled off in vacuo. Yield: 130 g (99% of theory) of benzoyl cyanide; melting point 32° C.

After purification, the distillation residue gave 225 g (99% of theory) of benzoic acid anhydride and 59 g of sodium chloride. The benzoic acid anhydride can be used for a further batch without purification.

EXAMPLE 2

295 g (1 mol) of 3-chlorobenzoic acid anhydride were mixed with 179 g (1 mol) of 3-chlorobenzoic acid chloride and 65 g (1 mol) of potassium cyanide and the mixture was slowly warmed to 190°–210° C. After the heat of reaction had subsided, the mixture was left at this temperature for a further 30 minutes and the potassium chloride was then removed by filtration. The filtrate was distilled. Yield: 162 g (98% of theory) of 3-chlorobenzoyl cyanide; boiling point 118°–120° C. at 14 mm Hg.

The 3-chlorobenzoic acid anhydride formed can be further used without purification.

EXAMPLE 3

93 g (0.5 mol) of pivalic anhydride were mixed with 60.5 g (0.5 mol) of pivaloyl chloride and 24.5 g (0.5 mol) of sodium cyanide and the mixture was slowly warmed to 100° C. After the exothermic reaction had subsided, the mixture was subjected to fractional distillation. Yield: 37.5 g (67% of theory) of pivaloyl cyanide, boiling point 47°–53° C. at 15 mm Hg.

The pivalic anhydride was recovered quantitatively.

EXAMPLE 4

132 g (0.5 mol) of 2,5-dichlorobenzoic acid anhydride, 105 g (0.5 mol) of 2,5-dichlorobenzoyl chloride and 32.5 g (0.5 mol) of potassium cyanide were slowly warmed to 150°–200° C. in a 500 ml flask, whilst stirring. The reaction was followed by IR spectroscopy. After conversion was complete, the mixture was subjected to fractional distillation (or, in the case of a further batch, to recrystallisation).

Yield: 97 g (97% of theory) of 2,5-dichlorobenzoyl cyanide, boiling point 142°–145° C. at 15 mm Hg.

130 g (98.5% of theory of 2,5-dichlorobenzoic acid anhydride were recovered after the distillation.

EXAMPLE 5

226 g (1 mol) of benzoic acid anhydride, 37.0 g (0.75 mol) of sodium cyanide and 48.8 g (0.25 mol) of benzotrichloride were warmed to 150° C. for two hours in a 1 liter flask. Towards the end of the reaction, the reaction mixture was clear and transparent. After cooling, it was subjected to fractional distillation. Yield: 97 g (98% of theory) of benzoyl cyanide, melting point 33° C.

168 g (99% of theory) of the benzoic acid anhydride employed were recovered; melting point 42° C.

EXAMPLE 6

339 g (1.5 mol) of benzoic acid anhydride, 50 g (98% pure, 1 mol) of sodium cyanide and 80.5 g (0.5 mol) of benzal chloride were warmed slowly, in the presence of 0.5 g of zinc chloride, to 130° C. and then to 160° C. in a 1 liter flask. The reaction had ended after 30 minutes. The reaction products were separated by distillation.

Yield: 125 g (96% of theory) of benzoyl cyanide; melting point 33° C.

EXAMPLE 7

226.2 (1 mol) of benzoic acid anhydride, 140.6 g (1 mol) of benzoyl chloride and 44 ml (1.1 mol) of anhydrous hydrocyanic acid were mixed and charged through a tube which was warmed to 230°–250° C. and filled with Raschig rings. The reaction product was collected in a flask and subjected to fractional distillation. Yield: 114 g (87% of theory) of benzoyl cyanide; melting point 32° C.

EXAMPLE 8

226 g (1 mol) of benzoic acid anhydride and 140.6 g (1 mol) of benzoyl chloride were stirred with 3 g of sodium benzoate for 10 minutes at room temperature. 50 g (1 mol) of 98% pure sodium cyanide were then added. This mixture was warmed to an internal temperature of 120° C. and, initially, an exothermic increase in the temperature to 136° C. took place. The reaction had ended after a stirring time of 3 hours at a temperature of 120° C. Working up gave the following yield: 127.5 g (96.5% of theory) of benzoyl cyanide; melting point 33° C.

EXAMPLE 9

72 g (0.5 mol) of sodium benzoate were mixed with 140.6 g (1 mol) of benzoyl chloride and 80 ml of tetramethylene-sulphone and 25 g (0.5 mol) of 98% pure sodium cyanide. After a stirring time of 20 minutes, an exothermic rise in the temperature to 85° C. was observed. It was now easier to stir the mixture. The subsequent reaction time was 2.5 hours at 150°–160° C. Working up gave the following yield: 65 g (99.3% of theory) of benzoyl cyanide; melting point 34° C.

It will be understood that the specification and examples are illustrative but not limitative of the present invention and that other embodiments within the spirit and scope of the invention will suggest themselves to those skilled in the art.

What is claimed is:

1. A process for the preparation of an acyl cyanide of the general formula

in which

R represents alkyl or substituted alkyl of from 1 to 8 carbon atoms, cycloalkyl or substituted cycloalkyl with 3 to 12 carbon atoms, aryl or substituted aryl; or an optionally substituted 5-membered or 6-membered heterocyclic radical which can also be fused with a benzene ring, which process comprises reacting a carboxylic acid anhydride of the general formula

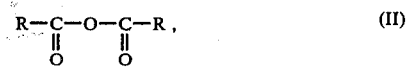

in which

R has the abovementioned meaning, in the presence of a compound of the general formula

in which

R has the abovementioned meaning, and

X represents a —COCl, —COF, —COBr, —CCl$_3$, —CF$_3$, —CBr$_3$, —CHCl$_2$, —CHF$_2$ or —CHBr$_2$ group, with an alkali metal cyanide or anhydrous hydrocyanic acid, at a temperature of between 50° and 300° C.

2. A process as claimed in claim 1 wherein R is alkyl of up to 4 carbon atoms.

3. A process as claimed in claim 1 wherein R is substituted alkyl of up to 4 carbon atoms wherein the substituents are selected from alkoxy of up to 4 carbon atoms, carbalkoxy of up to 4 carbon atoms in the alkoxy moiety, nitro, nitrile and halogen.

4. A process as claimed in claim 1 wherein R is cycloalkyl of 5 or 6 carbon atoms in the ring.

5. A process as claimed in claim 1 wherein R is substituted cycloalkyl of from 5 to 6 carbon atoms in the ring and wherein the substituents are selected from alkyl of up to 4 carbon atoms, alkoxy or carbalkoxy of up to 4 carbon atoms in the alkoxy moiety, nitro, nitrile and halogen.

6. A process as claimed in claim 1 wherein R is phenyl or naphthyl.

7. A process as claimed in claim 1 wherein R is substituted phenyl or naphthyl substituted with at least one substituent selected from alkyl of up to 4 carbon atoms, alkoxy or carbalkoxy of up to 4 carbon atoms in the alkoxy moiety, nitrogen and halogen.

8. A process as claimed in claim 1 wherein R is a heterocyclic radical selected from morpholinyl, imidazolyl, pyrazolyl, pyrrolyl, isoxazolyl, piperidinyl, oxazolyl, 1,2,4-triazol-1-yl, 1,2,4-triazol-4-yl, 1,2,3-triazolyl, 1,2,4-thiadiazol-2-yl, benzimidazolyl and furanyl.

9. A process as claimed in claim 1 wherein R represents straight-chain or branched alkyl of up to 4 carbon atoms or substituted alkyl of up to 4 carbon atoms wherein one or more substituents are selected from alkoxy of up to 4 carbon atoms, carbalkoxy of up to 4 carbon atoms in the alkoxy moiety, nitro, nitrile and halogen; cycloalkyl of from 5 or 6 carbon atoms in the ring system or substituted cycloalkyl of from 5 or 6 carbon atoms in the ring system wherein one or more substituents are selected from alkyl of up to 4 carbon atoms, alkoxy or carbalkoxy of up to 4 carbon atoms in the alkoxy moiety, nitro, nitrile and halogen; phenyl or naphthyl or substituted phenyl or naphthyl substituted with at least one substituent selected from alkyl of up to 4 carbon atoms, alkoxy or carbalkoxy of up to 4 carbon atoms in the alkoxy moiety, nitrogen and halogen; or a 5-membered or 6-membered heterocyclic radical which can contain 1 to 3 hetero-atoms, selected from oxygen, sulphur and nitrogen atoms in the ring and which may be substituted with substituents selected from alkyl of up to 4 carbon atoms, alkoxy or carbalkoxy of up to 4 carbon atoms in the alkoxy moiety, nitro, nitrile and halogen, and which can optionally be fused to a benzene ring.

10. A process as claimed in claim 1 wherein said carboxylic acid anhydride (II) is an aromatic carboxylic acid anhydride.

11. A process as claimed in claim 10 wherein said anhydride (II) is benzoic acid anhydride.

12. A process as claimed in claim 1 wherein the compound of the formula (III) is benzoyl chloride, benzotrichloride or benzal chloride.

13. A process as claimed in claim 1 wherein said alkali metal cyanide is sodium or potassium cyanide.

14. A process as claimed in claim 1 wherein said acyl cyanide is benzoyl cyanide and the said carboxyl acid anhydride is benzoic acid anhydride.

15. A process as claimed in claim 1 wherein said acyl cyanide is 3-chlorobenzoyl chloride and said carboxyl acid anhydride is 3-chlorobenzoic acid anhydride.

16. A process as claimed in claim 1 wherein said acyl cyanide is pivaloyl cyanide and said carboxyl acid anhydride is pivalic anhydride.

17. A process as claimed in claim 1 wherein said acyl cyanide is 2,5-dichlorobenzyl cyanide and said carboxyl acid anhydride is 2,5-dichlorobenzoic acid anhydride.

18. A process for the production of benzoyl cyanide comprising reacting an alkali metal cyanide with benzoyl chloride and benzoic anhydride in the presence or absence of an inert organic solvent.

* * * * *

UNITED STATES PATENT AND TRADEMARK OFFICE
CERTIFICATE OF CORRECTION

PATENT NO. : 4,284,584

DATED : August 18, 1981

INVENTOR(S) : Kurt Findeisen

It is certified that error appears in the above—identified patent and that said Letters Patent is hereby corrected as shown below:

Column 4, line 21, the "2" is omitted after the plus sign.

Column 4, line 25, delete the "2".

Column 10, line 19 "cyanide" not "chloride" before "and".

Signed and Sealed this

Ninth Day of March 1982

[SEAL]

Attest:

GERALD J. MOSSINGHOFF

Attesting Officer     Commissioner of Patents and Trademarks